(12) United States Patent
Morra et al.

(10) Patent No.: US 6,632,470 B2
(45) Date of Patent: Oct. 14, 2003

(54) METHODS FOR SURFACE MODIFICATION

(75) Inventors: Marco Morra, Asti (IT); Clara Cassinelli, Asti (IT); Linda Lee Cahalan, Nashua, NH (US); Patrick T. Cahalan, Nashua, NH (US)

(73) Assignee: Percardia, Merrimack, NH (US)

( * ) Notice: Subject to any disclaimer, the term of this patent is extended or adjusted under 35 U.S.C. 154(b) by 52 days.

(21) Appl. No.: 09/772,908

(22) Filed: Jan. 31, 2001

(65) Prior Publication Data

US 2003/0163198 A1 Aug. 28, 2003

(51) Int. Cl.[7] .............................. B05D 3/04; A61L 33/00
(52) U.S. Cl. ...................... 427/2.24; 427/2.1; 427/2.25; 427/2.28; 427/2.3; 427/2.31; 427/533; 427/488; 427/489; 427/490; 427/492; 427/534; 427/535; 427/536; 427/307; 427/322; 427/333; 427/407.1; 427/414; 427/415
(58) Field of Search ................. 427/2.1, 2.24, 427/2.25, 2.28, 2.3, 2.31, 533, 488, 489, 490, 492, 534, 535, 536, 307, 322, 333, 407.1, 414, 415

(56) References Cited

U.S. PATENT DOCUMENTS

| | | | |
|---|---|---|---|
| 4,267,202 A | | 5/1981 | Nakayama et al. |
| 4,508,606 A | | 4/1985 | Andrade et al. |
| 4,786,556 A | | 11/1988 | Hu et al. |
| 5,034,265 A | * | 7/1991 | Hoffman et al. ............ 427/2.25 |
| 5,132,108 A | | 7/1992 | Narayanan et al. |
| 5,169,675 A | | 12/1992 | Bartoszek-Loza et al. |
| 5,229,163 A | | 7/1993 | Fox |
| 5,229,172 A | * | 7/1993 | Cahalan et al. .......... 427/412.3 |
| 5,308,704 A | | 5/1994 | Suzuki et al. |
| 5,336,518 A | | 8/1994 | Narayanan et al. |
| 5,455,040 A | | 10/1995 | Marchant |
| 5,597,456 A | | 1/1997 | Maruyama et al. |
| 5,643,580 A | | 7/1997 | Subramaniam |
| 5,700,742 A | * | 12/1997 | Payne ......................... 442/123 |
| 5,723,219 A | | 3/1998 | Kolluri et al. |
| 5,782,908 A | | 7/1998 | Cahalan et al. |
| 5,962,138 A | | 10/1999 | Kolluri et al. |
| 6,013,855 A | | 1/2000 | McPherson |
| 6,159,531 A | * | 12/2000 | Dang et al. ................. 427/2.24 |
| 6,277,449 B1 | | 8/2001 | Kolluri et al. |
| 6,299,787 B1 | * | 10/2001 | Li et al. ........................ 216/34 |
| 6,440,166 B1 | | 8/2002 | Kolluri |

FOREIGN PATENT DOCUMENTS

| | | | | |
|---|---|---|---|---|
| EP | 0104608 B1 | * | 4/1984 | ........... C12N/11/00 |
| EP | 0 124 200 A2 | | 11/1984 | |
| EP | 0104608 B1 | | 3/1986 | |
| EP | 0941740 A2 | | 9/1999 | |
| EP | 1 088 564 A1 | | 4/2001 | |
| GB | 2 257 147 A | | 1/1993 | |
| WO | WO 97/22631 | | 6/1997 | |
| WO | WO 98/10116 | | 3/1998 | |
| WO | WO 00/48530 | | 8/2000 | |

\* cited by examiner

*Primary Examiner*—Shrive P. Beck
*Assistant Examiner*—Jennifer Kolb Michener
(74) *Attorney, Agent, or Firm*—Finnegan, Henderson, Farabow, Garrett & Dunner L.L.P.

(57) ABSTRACT

A method of modifying surfaces of a device, for example, a medical device, is disclosed. The method includes modifying a surface of a device by providing a device, exposing the device to a reactive gas and plasma energy to create a plasma deposited surface on the device, and quenching the device with the reactive gas. The device exhibits changes in its surface properties thereby making it more desirable for an intended use.

17 Claims, 2 Drawing Sheets

METHODS FOR SURFACE MODIFICATION

BACKGROUND OF THE INVENTION

The present invention relates to methods for surface modification. More particularly, the present invention relates to methods for surface modification of medical materials, such as, for example, biomaterials.

DESCRIPTION OF RELATED ART

For devices used in many fields, it is desirable to use materials having particular surface properties suitable for a given purpose so that the device optimally functions without causing adverse effects. One such field where it is desirable to have specific properties for the surface material of the devices is the medical field, where the surface characteristics of biomaterials are particularly important.

Biomaterials are typically made of inert metals, polymers, or ceramics to ensure durability. Furthermore, biomaterials are often desirably constructed of materials that do not adversely react with the physiological environment with which they come into contact, such as with blood or tissues. More particularly, many biomedical devices may or may not require blood compatible, infection resistant, and/or tissue compatible surfaces. For example, it is often desirable to manufacture medical devices, such as catheters, that have properties that discourage adherence of blood or tissue elements to the device. Conversely, it is also desirable for certain biomaterials, such as those for implants, to be anchored stably into the tissue environment into which they are implanted. For example, it may be desirable for specific implants, such as certain types of catheters and stents, to be non-inflammatory and anchored to the surrounding tissues. Moreover, it may be desirable for certain biomaterials to prevent bacterial growth during a course of a procedure, or as a permanent implant so as to prevent infection of a patient in contact with the biomaterial. For example, disposable surgical tools may become infected with bacteria during a course of a long operation and reuse of the tool during the operation may promote bacterial infection in the patient. For certain tools used in particular applications, it may be desirable therefore to prevent any bacterial growth on the surfaces of these tools during the course of an operation. Additionally for permanently implanted materials it would be desirable to prevent bacterial growth that would lead to a biomaterial or device centered infection. In the latter the only remedy is eventual removal of the implant. Thus, depending on the ultimate use of a biomedical device, it is often desirable to have the material surface property of a device vary according to a specific use.

To cause further advances in the biomedical field, the use of various materials should widen and their performance heightened by varying the surface properties of the material without changing its mechanical, optical, or other properties. For example, one type of biomaterial, polyolefin, can result in devices that have non-polar properties and therefore may result in poor adhesion, printability, and adaptability of its surface for coatings. Various kinds of surface treatments have been used to solve these promblems, such as corona discharge treatment, oxidation, flame treatment, surface grafting, irradiation, and direct plasma treatment. These methods have proven to have limited success due to their general ineffectiveness and expense.

Conventional techniques for coating a biomedical device with a desired surface layer typically are expensive, time-consuming, inconsistent in results, and do not ensure either a uniform layer of a surface material on the medical device or that the coating does not wear off in time. Thus, the properties of the surface layer of the device may vary between areas and thereby affect the overall surface property of the device. Furthermore, different devices subject to the same coating technique may result in different properties. Hence, there exists a need for a process that results in consistently reproducible and uniformly controllable surface conditions.

Another disadvantage of typical processes for applying a coating to a biomedical device is that each material requires a different technique to modify its surface. For example, metals, ceramics, and polymers have different surface properties and do not lend themselves to a common coating process. Polymers typically are hydrophobic or, at best, have relatively poor wetting, and therefore are difficult to coat from solutions. Furthermore, the majority of polymers used for medical devices also are relatively inert and do not possess functional groups that readily enter into direct chemical coupling reactions that could modify their surfaces. In order to overcome these limitations in polymers, surface treatments such as corona, plasma, irradiation, and chemical oxidation are used to make the surfaces more wet, or to add a functional group such as carboxyl (—COOH) or hydroxyl (—OH) to the surface.

Another important functional or reactive group that can be introduced to the surface is a free radical. This group can react with vinyl functional monomers to initiate chain reaction polymerization that results in a grafted surface. In yet another example, a polymer can be exposed to plasma treatment to generate surface free radicals. These free radicals however are short lived and lacking in surface density. Attempts to effect a chain reaction polymerization on such surfaces (graft) with monomers such as acrylamide only works on a few materials and poorly on those few materials. For example, a polyolefin material such as polypropylene may be exposed to air plasma activation, and then exposed to an acrylic monomer solution with catalysts. The results are a slight and patchy grafting with significant areas of no grafting. The reasons for these poor results have been explained by sighting two mechanisms. First, the plasma itself is a highly reactive state and so many radicals are produced that they end up reacting with each other, resulting in termination and/or neutralization of free radicals. A second mechanism is the reaction of the surface with oxygen from the air. This reaction leads to several additional degradative reactions that attack vinyl groups formed at the surface that also can be used for effective grafting.

With respect to plasma reactions, there are typically two types. First, there is plasma activation or plasma treatment with a gas that does not result in a deposition of new material to the surface. This reaction can do a number of things to the surface, including creation of new functional groups, ablation and/or cleaning of contaminants, and cross-linking. The second plasma reaction is called plasma polymerization or deposition. This is accomplished by the introduction of a reactive gas that can polymerize and/or react directly to the surface of the material. In the reaction of plasma polymerization or deposition, the resultant surface that is obtained on the material treated is dependent on the reactive gas used. For example, a polyethylene catheter may be treated with tetrafluoroethylene (TFE) gas resulting in a new surface with a polytetrafluoroethylene composition. This latter process is most often referred to as a "plasma polymerized" surface. The surface is most often a thin and conformal layer and is highly cross-linked. The surface differs considerably from a surface that has a layer generated by free radical initiated grafting. Free radical grafting takes place in the absence of the glow discharge of the plasma reactor and results in a non-cross linked layer. This property is advantageous when it comes to coupling additional molecules and especially biological molecules. The reason for this is that the grafted surface allows a more three dimensional network for these coupling reactions to take place as opposed to the highly ordered and rather two dimensional nature of plasma polymerized layers. This effectively results in the ability to have a higher loading of the coupled molecules to the surface as well as a greater degree of mobility and conformational integrity of the coupled molecules that helps maintain their natural bioactivity. Biomolecules require a mobile three-dimensional environment to react, and simple adsorption based on charge attraction results in a multipoint spread out attachment that compromises the conformational integrity of the molecule. The most practical application of this principle is in affinity chromatography.

Simple plasma activation of polymeric surfaces in order to subsequently generate a free radical initiated chain polymerized graft has several problems. The primary limitation is that the most common biomaterials such as PTFE (polytetrafluoroethylene), silicone, PVC (polyvinylchloride), metals, and ceramics do not effectively generate free radicals on their surfaces. With the remaining polymers such as urethanes, acrylates, polyolefins, and others, the plasma activation results in very different surfaces with respect to reactivity. An additional disadvantage to commercial polymers is the additives present contaminate the surfaces and make direct coupling to the native polymer unstable and unpredictable. Finally, free radicals generated on a polymeric surface by plasma treatment are short lived, and this makes it very difficult to attain optimal free radical grafted surfaces.

Plasma polymerized films can uniformly cover the surface of a polymer with a new composition, but these surfaces as mentioned previously are highly ordered, and attempts to further directly couple molecules at high loadings are difficult. Attempts to plasma activate a plasma polymerized film and subsequently free radical graft to this surface remove some of the disadvantages, but still suffer from the problems of short lived free radicals, and difficulty in adjusting plasma conditions to obtain optimal graft densities.

Thus, there exists a need for a relatively quick, economical, and universal method of treating a variety of types of surface materials to result in a stable coating having desirable biocompatible properties.

SUMMARY OF THE INVENTION

This invention is directed to methods of treating the surface of materials used for devices in any field, and to the related devices treated by such methods. Preferably, the method relates to the treatment of the surface of biomaterials, such as, for example, those used in medical devices. The treatment methods as disclosed in this invention are both suitable for medical devices that are used for an extended period of time, such as, for example, stents and other like conduits and devices, and also suitable for medical devices that are used for shorter periods, such as, for example, catheters.

Accordingly, the present invention is directed to methods that substantially obviate one or more of the problems due to limitations and disadvantages of the related art. To achieve these and other advantages and in accordance with the purposes of the invention, as embodied and broadly described, an aspect of the invention is drawn to a method of modifying a surface of a device. The method includes the steps of providing the device, exposing the device to a reactive gas and plasma energy to create a plasma deposited surface on the device, and quenching the device with the reactive gas.

The method may include the step of placing the device in a plasma chamber, and infusing air into the plasma chamber, wherein the placing and infusing steps occur prior to exposing the device to plasma energy.

In another embodiment of the invention, the invention is drawn to a method of modifying a surface of device. The method includes providing the device, placing the device in a plasma chamber, infusing air into the plasma chamber, exposing the device to air and plasma energy to clean the surface, exposing the device to a reactive gas and plasma energy to create a plasma deposited surface on the device, quenching the device with the reactive gas by infusing the plasma chamber with the reactive gas, removing the device from the plasma chamber and exposing the device to a surface grafting solution for preferably a relatively short period of time, such as less than one hour, to achieve a covalently bonded surface graft. A surface reactant species, such as a biomolecule, may then be coupled to the grafted surface.

In yet another aspect, the invention is drawn to a device used for medical procedures. The medical device has a surface modified by a surface treatment process. The process includes the steps of providing the device, exposing the device to a reactive gas and plasma energy to create a plasma deposited surface on the device, and quenching the device with the reactive gas.

Additional features and advantages of the invention will be set forth in the description which follows, and in part will be apparent from the description, or may be learned by practice of the invention. The objectives and other advantages of the invention will be realized and attained by the methods and devices particularly pointed out in the written description and claims hereof as well as the appended drawings. It is to be understood that both the foregoing general description and the following detailed description are exemplary and explanatory and are intended to provide further explanation of the invention as claimed.

BRIEF DESCRIPTION OF THE DRAWINGS

The accompanying drawings, which are incorporated in and constitute a part of this specification, illustrate preferred embodiments of the invention and, together with the description, serve to explain the objects, advantages, and principles of the invention. In the drawings.

DETAILED DESCRIPTION OF PREFERRED EMBODIMENTS

The method of the present invention generally relates to modifying the surface of a material. The method generally includes an initial step of exposing the material to plasma energy to clean and treat the surface so that a further layer may be plasma polymerized under exact conditions so that an even further layer may be grafted in an optimal manner. Next, free radical grafting to the plasma-polymerized surface is affected by exposure outside of the reactor to a solution of reactive monomers and catalysts. This result of successful grafting directly to the plasma polymerized surface is counterintuitive to the state of the art, and, in the preferred embodiment, is dependent upon following the steps given in FIG. 1 up to and including the free radical grafting step. As a further step, additional molecules and in particular, biomolecules, may be coupled to the grafted surface via numerous methods known, for example, in the field of affinity chromatography.

The present invention is designed to promote flexibility in surface properties in medical devices, particularly those that are in contact with a patient's body, including particularly those that are implanted in the body, such as stents. The invention, however, is not limited to treatment of devices that are implanted, and more broadly relates to methods of treating medical device surfaces to obtain desirable surface properties that maintain functional integrity for prolonged periods of time without causing detrimental effects in their surrounding environment.

The surface treatment process of the present invention has an advantage over conventional coating processes such that a treated material surface that has been subjected to the process of the present invention is stable and does not release or dissipate its altered surface condition.

Another advantage of the present invention over conventional coating techniques is that the present invention is universal. Conventional coating techniques are restricted by the device to be coated, that is, the techniques must be necessarily different for each material or device in order to modify its surface properties. However, the present invention is applicable to all types of materials and devices and, thus, makes it possible to treat a wide variety of materials and devices with the same process.

The coating methods of the present invention also result in uniform application of an altered surface property. Conventional surface coating procedures suffer from surface abnormalities and inconsistencies as a result of uneven distribution of surface coating during the coating process. These surface abnormalities affect the function of the materials and prevent uniform property characteristics. In contrast to conventional techniques, the process of the present invention produces a highly controlled and pure surface free from contaminants.

The inventive methods also allow the treated surface of a material, such as, for example, a medical device, to be layered with a particular substrate in order to give the entire device surface the property of the substrate. Stated by example, the process of the present invention enables a medical device to have a surface area that is covered by a particular substrate that alternatively may be connected to biologically-active species. Furthermore, as stated previously, a bioactive molecule can be attached to the grafted surface in an optimal manner through several well known affinity chromatography schemes to result in a high degree of conformational integrity and thus biological activity.

The methods of the present invention use the unique properties of plasma-polymerized surfaces and their ability, when generated by the method described in this invention, to promote optimal free radical grafted surfaces, and to perform such grafting without first treating the plasma-polymerized surface to additional plasma activation that is suggested by the state of the art. The methods also create conformal coatings that do not release the surface modification as is the case with common coating techniques. The method of the present invention creates a plasma deposited surface that can be directly grafted thereupon by using catalysts and vinyl monomers. Biomedical devices can, thus, be treated to be blood compatible, infection resistant, and tissue compatible.

Another advantage of the method of the present invention is that depositing a plasma film using a propylene gas onto a surface yields a treated surface that is capable of a direct and high density grafting that can be applied long after deposition, as long as, for example, up to and over one week post-deposition. The fact that a high-density graft can be applied directly after plasma deposition and without activation, and that this ability is long-lived is clearly counterintuitive to the teaching of the art. Observing the unexpected performance on non-activated control samples for plasma deposited films that were subsequently activated discovered this.

Reference will now be made in detail to the present preferred embodiments of the invention, examples of which are illustrated in the accompanying drawings.

Figure 1:
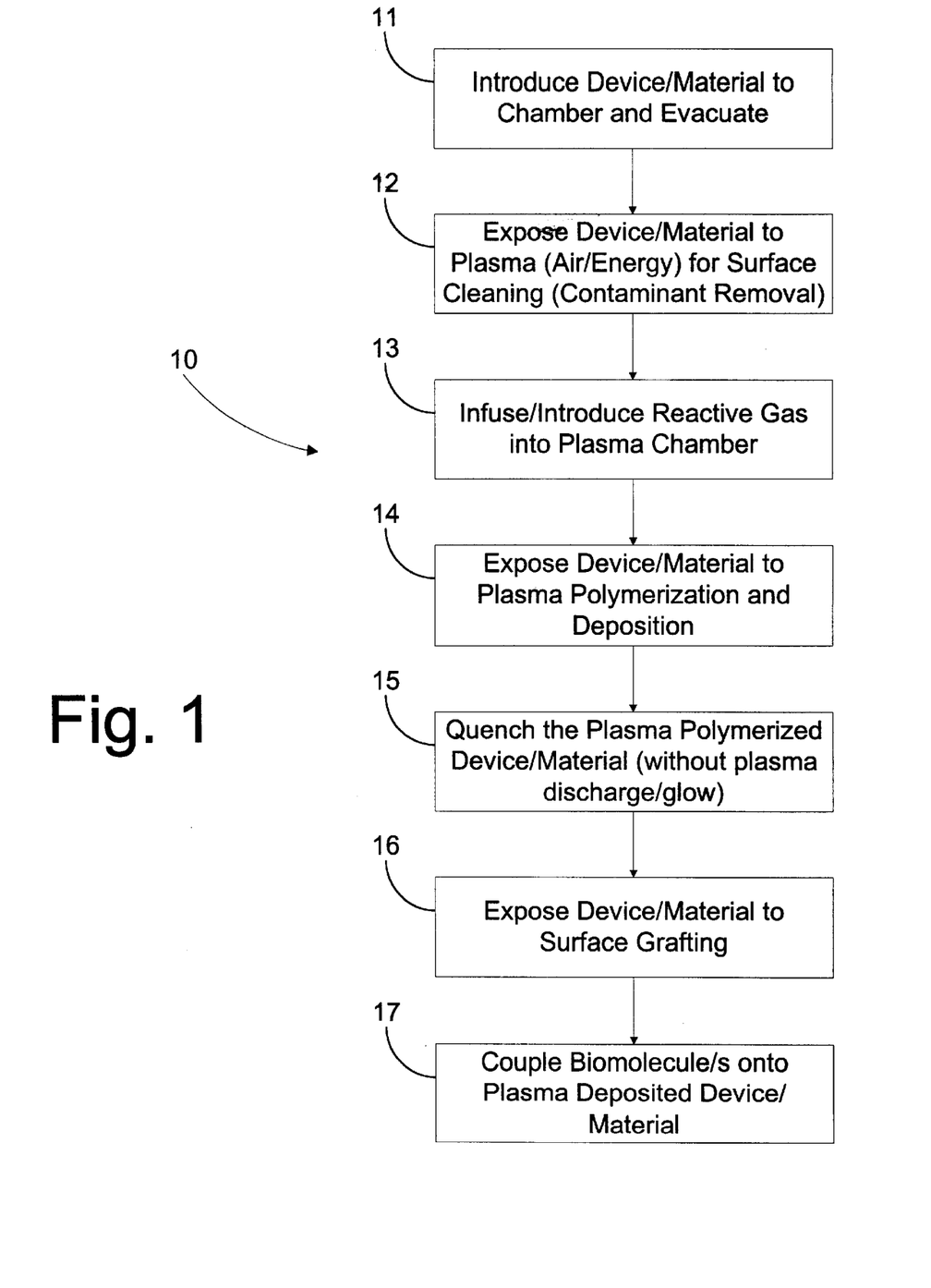
FIG. 1 is a flow chart describing a preferred embodiment of a method of the present invention.

An exemplary embodiment of the method of the present invention is shown in FIG. 1 and is designated generally by reference numeral 10. As embodied herein and referring to FIG. 1, the inventive method 10 comprises an initial step 11 of providing, or introducing, a device or material into a plasma chamber, and then evacuating the chamber. Throughout this disclosure, "device" and "material" are used interchangeably because the process of the present invention applies both to surfaces of materials and of course for surfaces of devices made of materials. Furthermore, each of steps 11–17 will be described in more detail below following an initial brief description.

Step 12 involves exposure of the device to plasma energy for cleaning and preparation for the step that involves plasma polymerization and deposition. Step 13 occurs after the energy has been turned off in the plasma reactor from Step 12, and includes the introduction of reactive gas into the chamber.

At Step 14, once the reactive gas flow has equilibrated, then the plasma energy is turned on to expose the device to plasma polymerization and deposition.

At Step 15, the power to the plasma reactor is turned off to prevent polymerization and deposition while the flow of reactive gas continues. This continued flow consumes (quenches) excessive and uncontrollable free radical reactions, and paradoxically leaves the surface more reactive to further grafting reactions, and for a relatively long period of time.

At Step 16, the material/device can be removed from the plasma reaction chamber and exposed immediately or at times even up to, for example, one week later to solutions of reactive monomers and catalysts for free radical grafting. This step can include a rigorous cleaning even at elevated temperatures to remove any unreacted monomers or non-permanently bonded species. This is yet another advantage of a grafted surface in that it can be rigorously cleaned and freed from any non-permanent or leaching species. Also, optionally, Step 16 may include any derivitization of the grafted surface such as coupling new functional ligands that have specificity for certain proteins, peptides, enzymes, cellular adhesive molecules, drugs, collagen, heparin, bactericides such as PHMB (polyhexamethylenebiguanide) and numerous other bioactive molecules.

Step 17 is the final attachment of the desired bioactive molecule to the grafted surface. Once again, this robust coupling mechanism can withstand rigorous cleaning attempts and present a verifiably stable surface with stable bioactivity which renders the device suitable for implant and contact with bodily fluids and tissues.

The method of the present invention is suitable for a wide range of materials and not limited to the medical field. The examples used in this specification will focus on the use of this method in the biomedical field, such as, for example, in treating common biomaterials including silicon, polymers including PE (polyethylene), PTFE (polytetrafluroethylene), DACRON (PET or polyethylene terephthalate), polyurethane (such as 80A), and PVC (polyvinylchloride), metals, such as stainless steel, nitinol (NiTi), tantalum (Ta), and titanium (Ti), ceramics, and other biomaterials known to one having ordinary skill in the art. Furthermore, the method of the present invention may be applied to inorganic, metallic, polymeric, and ceramic surfaces with equal ease and effectiveness.

The devices that are treatable with the method of the present invention include, but are not limited to, all medical devices, including without limitation catheters, probes, stents, tubes, screws, artificial implants, and orthopedic devices.

Figure 2:
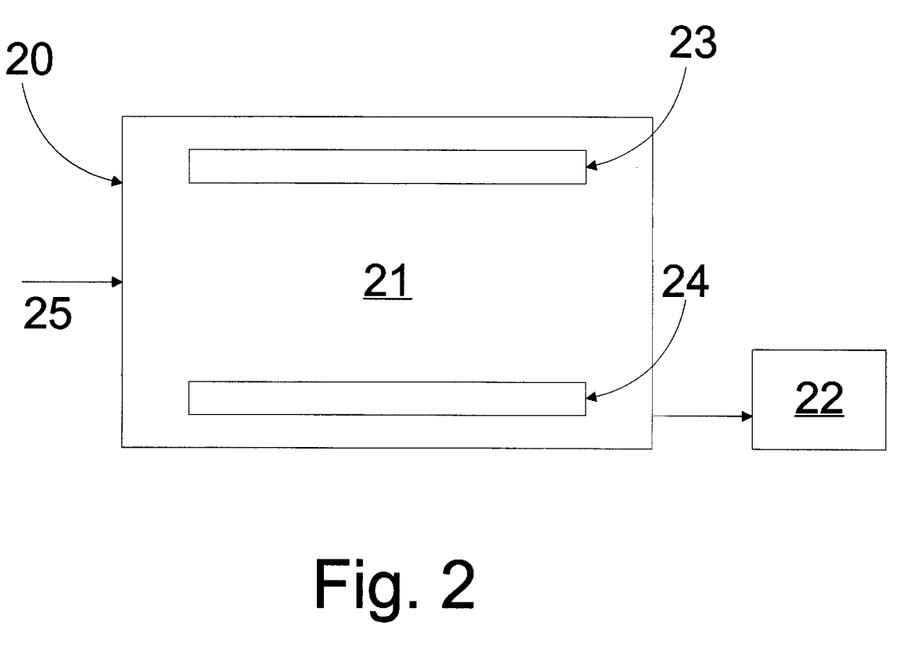
FIG. 2 is side view of a plasma chamber for plasma treating/depositing as used in a preferred embodiment of the present invention.

The general scheme of the plasma reactor is presented in FIG. 2. It is composed of a vacuum stainless steel chamber 20 with an interior 21 housing electrodes, including an upper electrode 23 and a lower electrode 24. The upper electrode 23 typically is polarized with radio frequency (anode); and the lower electrode 24 typically is grounded (cathode). The electrode diameter may be, for example, about 20 cm. The interior 21 should accommodate devices (not shown) placed within it for exposure to plasma energy.

Energy is coupled to the gas in the vacuum chamber 20 by a Radio Frequency matching network operating at, for example, 13.56 MHz. From the point of view of general classifications, a typical reactor such as this may be defined as a capacitatively coupled, RF parallel plate reactor, with internal electrodes. A suitable reactor is manufactured by Gambetti Kenolgia, Binasco (MI), Italy. That reactor has three different inlet lines for gases. An ENI ACG-3 XL generator may be used, preferably outside of the plasma chamber, sends current to the electrodes inside the chamber, and operates from 0 to 300 W of power. The electromagnetic energy, as used in Steps 12 and 14 of FIG. 1, may also be input by different coupling methods (inductive or capacitive), frequencies (DC, AC, radio frequency (RF), or microwave), and electrode configurations.

The embodiment shown in FIG. 2 presents an anode electrode 23 near the top of the chamber interior 21 and a cathode 24 near the bottom, but other positions for the electrodes are possible as long as there is sufficient space between the oppositely charged electrodes to generate charged gas species. The electrodes may have varying shapes and sizes. One preferred embodiment includes electrodes having 20 cm diameters. Alternatively, the electrodes 23 and 24 may be positioned outside of the chamber wall 20.

It is further desirable to provide a mechanism (not shown) for adjusting the relative position of the two electrodes 23 and 24 with respect to each other. The distance between the two electrodes 23 and 24 allows for varying control over generated ion species in the chamber 20, and also accounts for different sizes of devices placed within the chamber interior 21. Such an adjusting mechanism may utilize a screw technique, pneumatic, hydraulic, slide, or other such mechanism.

In operation, and according to Step 12 in FIG. 1, the plasma chamber 20 operates as follows to cause a surface change on a material placed therein. When a high frequency voltage is applied between the electrodes 23, 24, current flows into the chamber 20, forming a plasma, which glows. Reactive chemical species are formed in this electrical discharge. For example, the upper electrode 23 may be polarized with radio frequency (RF) energy and the lower electrode 24 is grounded. Energy is coupled to the gas in the vacuum chamber by a radio frequency matching network operating at, for example, about 13.56 MHz, and connected to the system by suitable known means.

A feed gas source 25 provides a stream of gases into the chamber 20. Gases may vary and include, for example, air or propylene. When the injected gas is air, as in Step 12, air plasma treatment introduces oxygen containing functionalities on the surface of polymeric devices positioned within the chamber interior 21. For example, hydroxyl, carboxyl, and other oxygen containing functionalities are introduced on the surface of polyethylene. As a consequence, the surface becomes more polar and wettability increases. Low molecular weight contaminants are effectively removed by the combined effect of plasma and vacuum. Air plasma treatment of metallic materials mostly exerts a cleaning effect, leading to the removal of hydrocarbon or, in general, organic contaminants from the metal surface.

When the injected gas is propylene, as in Step 14, the treatment allows for the deposit of a polymeric layer onto the substrate surfaces. Propylene molecules are fragmented in the plasma phase and recombine to yield a high molecular weight compound that deposits as a film on the device surface inside the chamber 20. The structure of the deposited film depends on the stream gas chemistry and the treatment conditions. Films deposited by this plasma process are, typically, highly cross-linked, pin-hole free, homogenous, and show good adhesion to the device.

In the present invention, films deposited by the plasma energy process where the infused source of gas 25 is propylene serve as a substrate for the grafting of other materials, such as acrylic acid (M) or acrylamide, which are typically added in a solution to which the substrate is exposed, as depicted in Step 16 FIG. 1.

Step 16 typically occurs outside the reactor 20 and involves exposure of the device from Step 15 to a reactive mixture for free radical graft polymerization. Typical reactive mixtures are aqueous solutions of acrylic monomers such as acrylic acid and acrylamide with appropriate catalysts. This step results in a permanent covalently bonded graft to the surface of the material. This graft is now ready for permanently coupling numerous classes of molecules and in specific conformations and controlled loading levels, as depicted in Step 17.

From here forward in this disclosure, when the feed gas source 25 is air, the treatment is called plasma treatment, and when the feed gas source 25 is propylene, the treatment is called plasma deposition.

All the variables for the chamber 20, including feed gas 25 injection rate and concentration, the power supplied to and distance between the electrodes 23 and 24, pump rate 22, and time of treatment/deposition are dependent on the size and nature of the device placed within the chamber interior 21, and are accordingly adjusted for optimal surface modification of materials placed within the chamber 20.

The invention will be illustrated by, but is not intended to be limited to, the following examples. For example, the method of the current invention also allows for covalent attachment via specific functionalities that permits specific loading levels, and optimal conformation of attached species. This feature is specifically important for attachment of antibodies, for example, where the complementarily determining region (CDR) of the antibody needs to be free for interaction with antigens. The only way to assure this is specific functional attachment schemes, and not random electrostatic attractive forces.

EXAMPLE 1

Plasma Treatment and Deposition on Short Polyethylene Tubes

A series of experiments were performed on small tubes to determine the effects of geometrical aspects (tube length) of the tube on the resultant plasma reactions. The tubes used were PE (polyethylene) tubes, 3 and 5 cm long, and with a 1.8 mm inner diameter. The tubes were placed into the plasma chamber described above and in FIG. 2. The plasma chamber was then operated by energizing the electrodes while gas flowed into the chamber, causing plasma formation. The flow rate of air into the chamber 20 was about 20 sccm (standard cubic centimeter per minute), obtained by opening the inlet valve so air could leak into the reactor. The distance between the electrodes 23, 24 was about 15 cm, but it has to be understood that the distance may be shorter or longer, for example, to about 5 cm. The power supplied was about 50 W. Decreasing the distance between the electrodes, while keeping all other variables constant, typically increased the density of the reactive species.

The duration of time during which a device was exposed to the plasma treatment and/or deposition was about 1.5 minutes to create a homogenous effect along the inner surface of the tubes. It is to be understood that shorter or longer exposure times may be suitable depending on a variety of factors, including the properties of the chamber and the device. These experimental conditions were found to be adequate to treat the inner lumen surfaces of tubes up to 5 cm. The surface effect of plasma treatment was clearly evident, as measured by significantly increased wettability of the interior of these tubes. Although both the inner and outer surfaces were treated, one surface may be easily "masked" as desired by suitable means known in the art.

The effect of the plasma treatment on surface chemistry of the inner lumen of the tubes was evaluated by wettability methods, and in particular by the capillary rise method. Such a method involves the measure of capillary rise, h, of a wetting liquid (such as water) in a capillary, given by the following equation:

$$h = (\cos\Theta) 2\gamma / (\rho g r),$$

wherein $\Theta$ is the wetting angle of water on the capillary surface, $\gamma$ is the water surface tension, $\rho$ is the water density, g is the gravitational acceleration, and r is the radius of the tube. Thus, for the same tube and the same liquid (water), capillary rise only depends on the wetting angle, which is the angle from horizontal that a line tangential to a drop of water on a surface makes from one side of the drop. Thus, as the wetting angle decreases, a drop becomes relatively more spread out on a given surface, and the surface is thereby more "wettable".

The wetting angle of water on PE is typically about 90 degrees, and so cos 90 is about 0, resulting in no capillary rise, and therefore poor wettability. Air plasma treatment decreased the wetting angle, so that a significant increase in capillary rise was observed.

After plasma treatment in air, the next step is plasma deposition with propylene gas. Thus, the tubes were then exposed to plasma deposition conditions, which is substantially the same as the plasma treatment conditions described above, but with propylene replacing air as the injected gas. Deposition from propylene plasma produced a hydrophobic hydrocarbon-like film with decreased wettability as compared to the post plasma treatment condition. The flow rate of propylene into the chamber 20 was about 105±10 sccm. The duration of plasma deposition was about 5 minutes to effectively cover the 5 cm long tubes. A 30 second quenching period followed the 5 minute deposition period. During the quenching period, propylene continued to flow into the chamber while the electrodes were not charged, hence no plasma deposition was being created during the quenching step. The quenching period allows active radicals to be quenched and the surface to become more uniform in deposition.

In general, the requisite time for plasma deposition is typically longer than the requisite time for plasma treatment. Tube length was found to play a more significant effect than in the case of air plasma treatment. A deposition time of 3 minutes was sufficient for 3 cm tubes but not for 5 cm tubes.

The resultant plasma deposited tube surfaces possessed a layer of propylene and exhibited reduced wettability, as compared with their plasma treated condition.

EXAMPLE 2

Copolymer Grafting of Stents

In another embodiment of this invention, copolymerization grafting was I performed on stents. The stents were initially pre-treated with plasma as generally described above in Steps 12–15. Then, to prepare a grafting solution, 70 g of a solution containing 35% distilled acrylic acid added to 120 g of deionized water to which 10 g of acrylamide had been dissolved. The resultant solution was then placed in a 300 mL glass vessel. After 2 minutes of stirring, argon gas was introduced with a slight bubbling into the solution. After 10 minutes, 6 ml of CAN (cerric ammonium nitrate) catalyst/initiator was added and allowed to stir with bubbling Argon for another 2 minutes after which the argon was discontinued. The premixed grafting solution was slowly dispensed into 10 ml glass tubes. The plasma-treated and plasma deposited stents were immersed into the solution and placed in an ultrasonic water bath (temp. about 18–25 degrees C). The total grafting time was about 40–45 minutes. After grafting, the substrates were extensively rinsed in deionized water followed with an overnight soak in deionized water at 50 degrees C. to remove any non-reacted monomer.

Next, the PEI coupling was performed. 8 ml of a 5% BASF PEI was combined with 200 g of 0.1 M borate buffer in a 250 ml beaker and allowed to stir for 30 minutes. The PEI solution was then dispensed into each (10 ml) tube containing previously grafted stents. Screw caps were secured on each tube then placed on a laboratory shaker at 80 rpm for about an hour. After PEI coupling the aminated tubes were rinsed with deionized water.

Finally, the nitrous acid degraded (NAD) heparin was prepared. A 0.2 g of NAD heparin was dissolved in the pre-mixed NaCl solution, then adjusted to pH 4.0±0.1. The solution was then preheated to 55 degrees C. After the solution reached the temperature, 0.02 g of $NaCNBH_3$ was added and allowed to mix for 9.0±1.0 minutes. Approximately 8.0 ml of the preheated heparin solution was dispensed into each tube containing previously grafted stents and control materials. Screw caps were secured on each tube then placed on a laboratory shaker. The shaker was placed in a 55 degrees C. oven and agitated at 80 rpm for 2 hours at 55 degrees C. After heparinization, stents and sample materials were rinsed with deionized water, 200 ml of 1 M NaCl adjusted to 4.0 pH, followed with a final deionized water rinse. The heparinized stents were allowed to air dry for three hours then were carefully remounted, inserted in blister packs, and into sterilization bags, ready for use.

EXAMPLE 3

Copolymer Grafting of the Present Method v. Other Methods

A study was performed to compare three sets of e-PTFE covered stents: the first group was subject to a preferred embodiment of the method of the present invention; the second group was subject to another known bioactive surface treatment method; and the third group (control) was not subject to any surface treatment.

Embodiment of Method of the Present Invention

The first group was subject to an embodiment of the method of the present invention substantially described in Example 2 above with some modification. The stents were initially cleaned by being subject to 1 minute of air plasma at 50 W and 20 sccm air flow rate into the plasma chamber. Next, the stents were subject to plasma deposition for 5 minutes under propylene plasma, at 50 W and 110 sccm propylene flow rate into the plasma chamber. A quenching period of 30 seconds followed the plasma deposition, wherein the electrodes were not activated, but propylene continued to flow into the plasma chamber. The treated stents were then set aside.

Next, a grafting solution was prepared. 30 g of acrylic acid (99% distilled, F.W. 72.06, Aldrich), 10 g of acrylamide (99+%, F.W. 71.08, ACROS), and 60 g of deionized water were weighed into a 200 ml glass vessel and stirred for 2 minutes. Argon gas was then introduced by slight bubbling reaction into the glass vessel. After 10 minutes, 0.1 M CAN (catalyst/initiator) was added and allowed to stir, by means of bubbling argon, into the solution for another two minutes. The argon was discontinued and the solution was slowly dispensed into small glass test tubes. The treated stents from Steps 11–15 were immersed into the solution-filled test tubes and placed in an ultrasonic water bath with a temperature of about 18–25 degrees C. for about 40–45 minutes. After this grafting process, the stents were extensively rinsed with deionized water.

Next, PEI was grafted onto the stents. 1.0 ml of 5% BASF PEI and 99 g of 0.1 M borate buffer (pH 9.0) were combined into a 250 ml beaker and allowed to stir for 30 minutes. Approximately 10 ml of the PEI solution was dispensed into each tube containing previously grafted stents. Screw caps were secured on each tube and then places on a laboratory shaker (Orbital) set at 80 rpm for 45 minutes. After PEI coupling, the aminated tubes were rinsed with deionized water.

As a final step, heparin was attached to the grafted stents. A nitrous acid degraded heparin ("NAD", 0.2 g) was dissolved in 200 ml of 0.5 M NaCl solution (adjusted to pH 3.9), and then adjusted to pH 4.0±0.1. The solution was then preheated to 55 degrees C. After the solution reached this temperature, 0.02 g of $NaCNBH_3$ was added and allowed to mix for 9.0±1.0 minutes. Approximately 10 ml of the preheated heparin solution was dispensed into each tube containing previously grafted stents. Screw caps were secured on each tube and then placed on a laboratory shaker (with the shaker placed into a 55 degree C. oven) at 80 rpm for 2 hours. After heparinization, the stents and sample materials were rinsed with deionized water, 1 M NaCl, and followed with a final deionized water rinse. The stents were then ready for thrombin experiments.

Other Known Method

The inventors of the present invention sought to compare the methods of the present invention with another method known in the art. The other method involves several adsorption steps relying on electrostatic charges for attachment versus covalent bonding. This renders the surface susceptible to removal under strong ionic rinsing as well as cracking of the coating on surfaces that undergo bending and flexing forces. Additionally, as stated previously, straight adsorption attachment does not allow for optimal loading and conformation as does the grafted layer of the present invention. Briefly, the other method known in the art involves alternating adsorbed surfaces of PEI and dextran sulfate with rinsing between each step. More than one adsorption step is required because, unlike the present invention, complete and uniform coverage of the surface is not sufficient in the adsorption approach. In the other method, a final layer of heparin is reacted to the electrostatically adsorbed layers.

Comparison of Two Methods

The e-PTFE covered stents prepared by the present invention and the existing commercial method described above were tested for thrombogenicity using a method described by Lindhout et al. in "Antithrombin activity of surface-bound heparin studied under flow conditions.", J. Biomed. Mater. Res., October. 1995, 29(10): 1255–1266, which is hereby incorporated herein in its entirety. The results showed that the amount of thrombin generated on a stainless steel e-PTFE covered stent coated according to the present invention (1.3 nM) was less than that generated on such a stent coated according to the other commercial surface method (7.0 nM). For comparison, the non-coated control surface displayed a thrombin level of 89.5 nM.

Furthermore, the same comparison of the present invention versus the other commercial method was made, but this time on a polyurethane surface. The results showed that the amount of thrombin generated on a Pellethane 55D Polyurethane material coated according to the present invention (0.4 nM) was considerably less than that generated on that material coated according to the other commercial surface method (35.5 nM). For comparison, the non-coated surface displayed a thrombin level of 53.0 nM.

Thus, improved resistance to thrombin generation was observed in the stents and materials treated according to the method of the present invention compared to those treated according to an existing commercial method, although both methods showed dramatic improvement in thromboresistance as compared to untreated controls.

In addition to the above showing of improved thromboresistance, the consistency of performance on different materials can be seen with the present invention. The present invention takes advantage of the high degree of control and uniformity in applying a plasma deposited layer to all materials, and the ability under the conditions of this invention to obtain a high density graft to this surface. A final advantage of the present invention is a simpler process requiring fewer solutions and not subject to numerous adsorption layers susceptible to non-specific adsorption phenomenon that are difficult to control.

EXAMPLE 4

Surface Deposition of Adhesion Molecules

Collagen exhibits excellent cell adhesion properties, promotes natural wound healing, and stimulates fibroblast adhesion and growth. Thus, it would be beneficial to deposit collagen upon surfaces of certain medical devices to promote incorporation of the device into the body tissues. The present inventors have discovered that collagen may be covalently bonded to an acrylic acid (AA) substrate surface. Devices that have collagen grafts exhibit excellent cell adhesion properties.

As an example of collagen grafting, the present inventors used glass slides to provide a method for grafting collagen onto a material. First, acrylic acid (AA) grafted slides were prepared as generally described above, and further subjected to collagen coupling. Collagen was supplied (by Biophil Chimica Fine sri, Vimodrone (MI), Italy) as a 1% collagen native solution. This is a soluble collagen obtained from fresh calf skin. The extraction is done very carefully to avoid any denaturation of the collagen molecules. The average molecular weight is more than 285000 D. The product is US registered.

The coupling was performed as described herein. AA grafted glass samples were immersed in a 0.5% collagen, 1% acetic acid aqueous solution. After 2 hours, samples were removed from the solution and rinsed several times in 1% aqueous acetic acid to remove excess adsorbed collagen. After rinsing, collagen was covalently coupled to the graft by immersing the samples in water containing 0.5% N-(3-dimethaminopropyl)-N'ethylncarbodiimide hydrochloride (EDC) and 0.5% N-hydroxysuccinimide (NHS), both form Sigma, and kept overnight in this coupling solution. Before analysis, all samples were carefully rinsed and dried under a hood. Microscopic analysis (using atomic force microscopy (AFM)) of the surface of a standard glass slide, an AA grafted surface, and a collagen-coupled surface revealed remarkable differences in surface topography. The glass surface was typically very smooth. The AA grafted surface revealed many large and small bumps on the surface. Thus, the surface area of the slide had increased due to the many bumps formed. Finally, collagen coupling to the AA surface increased the surface area even greater than glass alone or AA grafted glass, thereby creating even a larger surface area for interaction with the surrounding environment. Collagen appears to fill in the valleys between the large bumps of the AA grafted surface. The increased surface area and stiffness of the collagen-coated surface promotes the attachment of fibroblasts and other cells on it.

Observations of fibroblast cell growth behavior clearly revealed major differences between samples of AA grafted and collagen-coated AA grafted surfaces. The former surface was a poor substrate for cell adhesion. Cells failed to spread out, and after a few hours, formed clusters on the AA surface. These clusters became preferential sites for cell adhesion and, as a consequence, colonization of the surface by cells was spotty, with large clusters and ample empty areas.

The collagen-coated AA grafted surface however yielded dramatically different results than the AA grafted surfaces. When collagen coating is added, a complete and homogenous layer of cells' is observed. Clearly, the top-most collagen layer has a very significant effect in terms of the interaction between the fibroblasts and substrate. The cell layer is definitely confluent and no empty spaces or non-homogeneous colonization is observed. There are several advantages for a complete confluent layer of fibroblasts. One advantage is anchorage of tissue to the surfaces of biomaterial, which can lead to protection from infection, and minimization of scar tissue formation.

Use of the present invention results in greater growth rates for cells, such as osteoblast-like cells (such as MG-63 osteoblast-like cells from a human osteosarcoma), on AA grafted collagen coupled titanium. Osteoblast-like cells grow significantly more on an AA grafted titanium or an AA grafted collagen coupled titanium surface using the method of the present invention as substantially described above than when the osteoblast-like cells are placed directly on a control titanium surface. This result confirms that collagen-coating of a surface using the method of the present invention promotes the normal adhesion and proliferation of cells on the surface.

EXAMPLE 5

Modifying Surfaces to Prevent Cell Adhesion

Using the methods of the present invention, the surfaces of medical devices not only may be modified to promote cell growth thereupon, as described in the above examples and discussion, but may also be modified to prevent cell growth or even promote cell destruction. Another type of coating using the method of the present invention includes creating a biocidal surface by grafting PHB (poly(hexamethylene biguanide hydrochloride)) onto an acrylic acid grafted surface. PHB is a powerful cationic biocide. It can be coupled to the anionic AA grafted surface. This surface remains stable upon storage in aqueous environments.

Grafting of an exemplary glass surface was performed using the method as generally described above and specifically described in Example 4. PHB, from a 20% aqueous solution, was coupled ionically to AA grafted surfaces and to collagen coated AA grafted surfaces. Coupling was performed by immersing the glass samples in a 2% PHB solution for two hours.

Exposer of the PHB coated glass surface to a bacterial solution of *Staphylococcus epidermidis* RP62A (ATCC 35984) showed the biocidal effect of PHB. After 6 hours of exposure, a significant biocidal effect was observed.

PHB coating increases adhesion of *S. epidermidis* to the AA grafted surface on the short term. This result likely reflects the contribution of electrostatic attraction between the positively charged PHB surfaces and the negatively charged bacterial cell wall. The PHB acts as a type of "bacterial trap", attracting bacteria via electrostatic and hydrophobic (PHB surfaces are less wettable than AA grafted ones) interactions. The PHB surface was effective in killing 97% of the bacteria after 6 hours of exposure. PHB coated surfaces were found to be generally stable, with results showing that PHB was still evident even after 6 days of storage in PBS solution.

Although the invention has been described with the preferred embodiments shown, other embodiments are also within the teaching of this invention. For example, besides the use of propylene, grafting was also successfully performed with saturated propane, or tetramethyldisiloxane. These and other changes to the method and devices described are possible without detracting from the teachings disclosed herein.

We claim:

1. A method of modifying a surface of a device, comprising:
    providing the device;
    exposing the device to a reactive gas and plasma energy to create a plasma deposited surface on the device, the reactive gas being chosen from propylene, propane, and tetramethyldisiloxane; and
    quenching the device with the reactive gas.

2. The method of claim 1, further comprising, prior to the exposing step, the step of exposing the device to air and plasma energy to clean the surface.

3. The method of claim 1, further comprising the steps of:

placing the device in a plasma chamber; and infusing air into the plasma chamber, wherein the placing and infusing steps occur prior to exposing the device to plasma energy.

4. The method of claim 3, wherein the quenching step includes infusing the plasma chamber with the reactive gas.

5. The method of claim 1, further comprising the step of:

exposing the device, after the quenching step, to a surface graft material to bind the surface graft material to the plasma deposited surface.

6. The method of claim 5, wherein the surface graft material is acrylic acid.

7. The method of claim 6, wherein the surface graft material includes acrylamide.

8. The method of claim 5, further comprising the step of:

coupling a surface reactant species to the surface after the surface graft exposure step.

9. The method of claim 8, wherein the surface reactant species is heparin.

10. The method of claim 8, wherein the surface reactant species is collagen.

11. The method of claim 8, herein the surface reactant species is poly(hexamethylene biguanide hydrochloride).

12. The method of claim 5, wherein the device is exposed to the surface graft material without a plasma activation step occurring after the quenching step.

13. The method of claim 12, wherein the device is exposed to the surface graft material over 12 hours after the quenching step.

14. The method of claim 12, wherein the device is exposed to the surface graft material over 48 hours after the quenching step.

15. The method of claim 1, wherein the device is a medical device.

16. A method of modifying a surface of a medical device, comprising:

providing the medical device;

placing the medical device in a plasma chamber;

infusing air into the plasma chamber;

exposing the medical device to air and plasma energy to clean the surface;

exposing the medical device to a reactive gas and plasma energy to create a plasma deposited surface on the device, the reactive gas being chosen from propylene, propane, and tetramethyldisiloxane;

quenching the medical device with the reactive gas by infusing the plasma chamber with the reactive gas;

exposing the medical device to a surface graft material to bind the surface graft material to the plasma deposited surface; and coupling a surface reactant species to the grafted surface.

17. The method of claim 16, wherein the medical device is exposed to the surface graft material over 12 hours after the quenching step.

* * * * *

UNITED STATES PATENT AND TRADEMARK OFFICE
CERTIFICATE OF CORRECTION

PATENT NO. : 6,632,470 B2  
DATED : October 14, 2003  
INVENTOR(S) : Marco Morra et al.

It is certified that error appears in the above-identified patent and that said Letters Patent is hereby corrected as shown below:

Column 15,
Line 14, replace "claim 6," with -- claim 5, --.

Signed and Sealed this

Twenty-seventh Day of January, 2004

JON W. DUDAS
*Acting Director of the United States Patent and Trademark Office*